United States Patent [19]
Acharya

[11] Patent Number: 5,102,666
[45] Date of Patent: Apr. 7, 1992

[54] CALCIUM POLYCARBOPHIL CONTROLLED RELEASE COMPOSITION AND METHOD

[75] Inventor: Ramesh N. Acharya, Lake Forest, Ill.

[73] Assignee: Oramed, Inc., Mundelein, Ill.

[21] Appl. No.: 580,854

[22] Filed: Sep. 11, 1990

[51] Int. Cl.⁵ .............. A61K 47/32; A61K 9/10; A61K 9/26; A61L 19/24
[52] U.S. Cl. .................... 424/487; 424/484; 424/440; 424/441; 424/457; 424/462; 424/470; 424/474; 424/435; 424/443; 424/422; 424/501
[58] Field of Search .......... 424/484, 81, 487

[56] References Cited

U.S. PATENT DOCUMENTS

| | | | |
|---|---|---|---|
| 3,640,741 | 2/1972 | Etes | 106/170 |
| 4,029,815 | 6/1977 | Sherlock et al. | 514/575 |
| 4,140,763 | 2/1979 | Bachrach et al. | 424/89 |
| 4,615,697 | 10/1986 | Robinson | 604/890 |
| 4,867,979 | 9/1989 | Sheth et al. | 514/867 |
| 4,900,552 | 2/1990 | Saavordeker et al. | 424/422 |
| 4,988,679 | 1/1991 | Chavkin et al. | 514/53 |

*Primary Examiner*—Thurman K. Page
*Assistant Examiner*—Edward J. Webman
*Attorney, Agent, or Firm*—Leydig, Voit & Mayer

[57] ABSTRACT

Controlled release compositions comprising calcium polycarbophil and an active agent selected from the group consisting of medicinal agents, breath fresheners, and flavors, and a method of controlled release of such an active agent.

14 Claims, No Drawings

CALCIUM POLYCARBOPHIL CONTROLLED RELEASE COMPOSITION AND METHOD

BACKGROUND OF THE INVENTION

This invention relates to certain pharmaceutical dosage forms, and in particular to certain polymeric matrices or complexes which are suitable for achieving controlled or sustained delivery of an active composition. The compositions are especially useful for local, parenteral, buccal, gingival, and oral controlled release of active compositions and take the form of granules, encapsulated capsules, tablets, chewable gums, ingestible and implantable boluses, candies, lolipops, pourable liquids, gels, suppositories and the like.

BACKGROUND OF THE INVENTION

Delivery of pharmaceutical compositions through the use of polymeric carriers is a well known technique. Robinson U.S. Pat. No. 4,615,697 provides an excellent review of this subject, especially as it relates to the use of bioadhesive compositions for buccal administration. The buccal delivery systems disclosed in Robinson utilize known bioadhesives to hold the polymeric system in place in the buccal cavity after insertion therein. The drug is released from a bioadhesive matrix and absorbed into the buccal lining. The compositions disclosed in Robinson provide a means of trans-mucosal delivery of therapeutic agents that are subject to poor bioavailability due to solubility limitations, polarity considerations, degradation due to pH, enzymatic exposure or "first pass" metabolism by the liver or gastrointestinal enzymes after oral ingestion. However, such delivery systems, although of general utility have certain disadvantages in actual application. U.S. Pat. No. 4,900,552 provides a composition for releasing active ingredients in the buccal cavity itself for an extended period of time. The composition of that patent comprises a trilaminate film segment capable of delivering an active ingredient within the buccal cavity while attached to a wall of that cavity. The trilaminate film segment includes a hydratable bioadhesive base layer, a non-adhesive reservoir layer and a water-impermeable barrier sandwiched between and bonded to the base layer and the reservoir layer. Such a composition is by its very nature a complex structure requiring detailed formulation techniques to achieve the desired composition.

Alginic acid, including its salts, has also been used in various forms and combinations for purposes of providing bioadhesive compositions for the administration of active compositions. As one example thereof, the use of cross-linked alginate gum gel is described in Etes U.S. Pat. No. 3,640,741 as being suitable for use as the bioadhesive.

As an alternative to the bioadhesive approach, lozenges, candies, lolipops, chewing gums and the like are often used to deliver active compositions. Typically there is entrained an active agent in a slowly dissolving or disintegrating material, such as common and complex carbohydrates, starches, natural and synthetic polymers and the like. With respect to the types of delivery systems which rely on solvation or disintegration, the active composition is released as the matrix dissolves or disintegrates after contact with the saliva.

For chewing gum delivery systems, a rubber-like polymer, such as a polybutadiene typically is used, which does not dissolve nor disintegrate in the mouth. Release of the active composition is through diffusion and migration of the active composition through the polymeric matrix to the surface of the product as a result of the chewing and mastication action, causing ultimately mixing of the active composition with the saliva.

Both of the aforementioned types of delivery systems have the disadvantage that the rate of release of the active composition is highly dependent upon the chewing action of the individual. Further, the presence of sugars and the chewing action stimulates saliva secretion which in turn results in limited effective release times. Further, the presence of high levels of sugars in the formulations promote bacterial growth and cause dental and peridontal diseases.

Because of all of the foregoing shortcomings in the prior art delivery methods, a need has existed for a delivery system suitable for oral, buccal and gingival delivery of active compositions that overcomes such deficiencies in the prior art systems.

There is also a considerable interest in developing controlled release delivery systems suitable for parenteral applications. A variety of sophisticated approaches such as biodegradable implants, liposomes, injectable microspheres, injectable microsponges, and "self depot" injections have been reported in the literature. In all of these types of controlled release delivery systems, there are numerous limitations. A need has existed for delivery systems which can be manufactured easily and administered parenterally using currently available administration systems. With the present invention it is possible to design a delivery system which is fluid at the time of injection but polymerizes in the body to form a hydrogel matrix, to achieve controlled release of active ingredients over a period from a few days to many months.

Burn treatments and wound healing applications require special delivery systems for local application of active agents. In these conditions the affected local area is highly compromised and minimum additional trauma can be tolerated. Liquid preparations, sprays, gels, medicated bandages and liquid skins have been reported in the literature to provide controlled local delivery of active agents, each in their own deficiencies. Additional requirements are introduced by many dermatological and ophthalmic conditions e.g. psoriasis, dermatitis and ocular infections and the like, which require controlled delivery systems for a specific site or for a large area of the body, for local pharmacological actions.

Another application area of concern is the site specific and target-organ delivery of chemotherapeutics and radiological agents. Effective treatment in these applications require achievement of a very high concentration of active agent in specific sites, e.g. tumor cells, hyperactive glands and the like. "Depot" delivery or "delivery depot" processed by external devices, such as magnetic focusing are reported to contain the drug within the target organ but the complexities of the known techniques introduce additional undesirable complications and requirements.

SUMMARY OF THE INVENTION

The present invention provides a polymeric delivery system which is formed through the interaction of a calcium polycarbophil type composition with water and/or other cosolvent. The resulting product is especially useful as a carrier or coating of active compositions, such as pharmaceuticals and the like, and as a coating for pharmaceutical excipients, actives and intermediate products, to retard dissolution of a substrate e.g. granules, sugar crystals, tablets and the like, and provides a means for achieving a rate-controlled release of the active composition.

The present invention provides several advantages and benefits, including an improved composition and method for the controlled release of an active composition to oral, buccal or gingival skin or mucosa over a period of time. The compositions are not noticeably irritating to the skin or mucosa with which they are contacted and they may contain substantially any medicinal agent or cosmetic agent.

The present invention also provides a method of controlled release treatment by use of a polymeric carrier containing a therapeutically effective amount of an active composition, wherein the polymeric complex carrier is formed by the interaction of a calcium polycarbophil type component with water in the presence of the active composition, and is then used to contact an area of skin or mucous membrane to be treated with said active composition, for a sufficient period of time to allow a therapeutically effective amount of said active composition to be released from the complex.

The present invention also provides a method of controlled release treatment through use of a polymeric carrier and a therapeutically effective amount of an active composition which is a "complex hydrogel" that is formed within the body after it is administered, to provide controlled release of an active agent from the matrix over the course of a few days to a few months.

The composition is supplied as a two part system, a polymer phase and a liquid phase. Upon reconstitution of the two phases, the system initially remains in a fluid state to allow its delivery intramuscularly. Once injected, it forms a highly structured hydrogel matrix within short time to provide a controlled delivery of active agents, such as drugs dispersed within the matrix.

The present invention also provides a delivery system for controlled release a local applications. The treatment comprises of pourable preparation which sets within a few seconds after it is applied locally. The delivery system consists of a two part system which comprises a polymer phase and a liquid phase. The active medicinal agents may be present in either or both the phases. The two parts may be thoroughly mixed to initiate complexation. Some preparations of the present invention may have a thick consistency, enabling them to be poured over the area to be treated, forming a controlled release hydrogel system. Such a system allows the drug dispersed within the matrix to diffuse to the local site of application. Because of the hydrogel nature of the matrix, the protective barrier allows free diffusion of materials from the local sites into the matrix and thus behaves as a breathable protective barrier.

The present invention also provides a method of targeting administration of chemotherapeutic agents and radiologicals at the desired sites, e.g. cancerous tumors, hyperactive glands, and the like. The system consists of a two-part system, a polymer phase and liquid phase. When the two parts are mixed together, the system remains fluid for a short period of time to allow its administration. Once at the site of application, it completes its internal structuration to form a complex hydrogel matrix containing the active drug within the area of the target site. The polymeric delivery system comprising calcium polycarbophil and other excipients, along with active agents, may be formulated with nonpolar solvents and cosolvents to maintain its fluidity. Once injected, intercellular and/or intracellular water will penetrate and activate the hydrogel matrix formations to achieve controlled drug delivery systems.

With the present invention it is possible to design a delivery system which is fluid at the time of injection but polymerizes in the body to form a hydrogel matrix, to achieve controlled release of active ingredients over a period from a few days to many months.

Other benefits and advantages of the present invention will be apparent to those skilled in the art from the Detailed Description, Examples and Claims that follow.

DETAILED DESCRIPTION OF THE INVENTION

The present invention relates to a polymeric delivery system which may be used as controlled release carriers, and to methods for the use of such systems. The delivery systems of the present invention are formed through interaction of a calcium polycarbophil type composition with water. Preferably, the calcium cation is initially present in the form of a salt with the polycarbophil type composition. The compositions also include an effective amount of an active composition which is incorporated in the polymeric matrix.

The matrix of the present invention provides the controlled release effect by forming a complex hydrogel which is gum/sponge-like in consistency and retards the dissolution and diffusion of the active ingredient from the matrix which, for example, may be in the form of a tablet, lozenge, candy, granule, suppository or the like. The hydrogel matrix system may be formed at the time of application and such an approach is especially useful for treating dermatological and ocular disorders, as through burn and wound healing treatments, ocular infections, and ocular inflammations, and for providing parenteral or local application of active agents.

Calcium polycarbophil, upon contact with water and optionally with a cosolvent, sets in a matter of a few minutes into a cohesive hydrogel material which may be either a rubbery mass, or a highly rigid mass, for example, if the requisite amount of water is added. Such a cohesive material may be of rubber/sponge-like consistency and does not have any inherent taste nor odour. Further, the composition does not readily dissolve nor disintegrate when exposed to saliva and can withstand a mild amount of chewing or mastication. Further, the composition can control the release of soluble materials by retarding their dissolution and diffusion within and from the matrix.

The resulting matrix of calcium polycarbophil and water may be a polymeric hydrogel matrix which may be formed, as by cutting, into small pieces of appropriate size and shape. The resulting product can be dried to any degree of hardness and moisture content. As an alternative, the calcium polycarbophil may be mixed with other excipients and active agents, and mixed with water and other cosolvents, granulated, dried to a desired initial dry weight moisture content and tableted using conventional tableting procedures. The resultant products may be molded into lozenges, suppositories or gums, for example; encapsulated into gelatin capsules; compressed into tablets; ground into dry powders or granules and may be further coated, if desired.

Additionally, the compositions of the present invention when formed at the time of administration may be used as in the form of an ingested or implanted bolus, as through parenteral injection, which upon administration will controllably release the active composition with passage of time only.

The controlled release rate of the active agent is dependent upon the structure of the hydrogel matrix which may be modified through use of polar and non-polar cosolvents and their amounts and the inclusion of other components, e.g. carbohydrates and hydrocolloids which act to modify the physical and chemical properties of the matrix. For example, an auxiliary hydrocolloid may be employed, such as cellulose polymers which are cellulose ethers such as methyl cellulose, cellulose alkyl hydroxylates such as hydroxypropylmethyl cellulose, hydroxypropyl cellulose, hydroxymethyl cellulose or hydroxyethyl cellulose, cellulose alkyl carboxylates such as carboxymethyl cellulose and carboxyethyl cellulose, and alkali metal salts of cellulose alkyl carboxylates, such as sodium carboxymethyl cellulose and sodium carboxyethyl cellulose, as well as carboxypolymethylene (molecular weight 2.5 to 3.5 million), gum acacia, guar gum, gum tragacanth, gum xanthan, alkali metal or alkaline earth metal carageenates, and alginates, such as alginic acid, ammonium or sodium alginate or mixtures thereof. Simple or complex carbohydrates or polyols, such as sucrose, xylose, mannitol, glucose, starch, Pluronic surfactants, and the like may also be employed to modify the hydrogel stucture.

The interaction of the calcium polycarbophil, optionally in the presence of a hydrocolloid or polyols or cosolvents, with water results in the formation of a hydrogel complex of varying solubility which affects the dissolution of the active agent out of the matrix. The controlled release rate of the active agent is dependent, in part, upon the quantity of water and other cosolvents initially present to form the complex, and in part upon the interaction of the polymer and other excipients, including the hydrocolloids, and/or carbohydrates if present. Active agents, such as medicaments, may be released by diffusion or leaching through the sponge matrix or by errosion of the matrix. An active agent, such as a medicament, may be released in a controlled manner for extended periods up to several months. Typically, the duration may be for several weeks, in the case of implanted boluses and the like, to several days, such as from 1 to 3 days. In orally administered chewable products, the duration of release usually is for at least about four to twelve hours, and typically for about one-half hour or more.

The controlled release compositions of the present invention will include an active agent in an amount within the range of from about 0.0001 to about 65% by weight, preferably in an amount within the range of from more than 0.001 to about 35% by weight of the composition. The calcium polycarbophil polymer will be present in an amount within the range of from about 0.01 to about 99%, and preferably from about 0.25% to about 50% by weight of the composition; and the auxillary excipients may be present in an amount within the range of from about 0.01 to about 99%, and preferably from about 0.25 to about 50% by weight of the composition. Water will typically be present in an amount of about 5 to about 200% and preferably from about 10 to about 100%, based upon the weight of the calcium polycarbophil. The amount of water added may vary depending upon whether other excipients are present. The water content as described herein is the amount added to initiate the formation of a hydrogel. Once the gel is formed, the water may be removed to obtain a dry powder, granules or a matrix, or more water may be added to obtain the desired consistency.

The sustained release matrix will optionally include additional edible non-toxic ingredients as conventionally employed in medicinal dosage forms. Thus, the compositions of the invention may optionally include one or more excipients in an amount within the range of from about 0.1% to about 99% by weight and preferably from about 1% to about 95% by weight, such as lactose, sugar, corn starch, modified corn starch, mannitol, sorbitol, and inorganic salts such as calcium carbonate. Other conventional ingredients which may optionally be present include preservatives, stabilizers, plasticizers, cosolvents, anti-adherents or silica flow conditioners or glidants, such as Syloid brand silicon dioxide as well as FD&C colors.

The compositions of this invention are substantially non-toxic to the animals in which or on which they are placed, aside from any toxicity associated with the active composition alone. Thus, when contacted with and adhered to skin or mucosa, the compositions cause no apparent whitening or blistering effects due to the compositions. In addition, adverse immunologic effects from the use of compositions of this invention in animals should not be present.

The phrases "pharmaceutically acceptable", "physiologically tolerable" and "medicinally inert" are used herein to mean that the material so described may be used for treatments in or on humans or other mammals without causing ill effects, such as toxicity, blistering or whitening of mucosa or skin tissues, and that those materials are not themselves active compositions or bioadhesives, as those terms are used herein.

ACTIVE COMPOSITIONS

The active compositions useful herein are selected generally from the classes of medicinal agents. Substantially any such agent may be used in the present invention including both solid and liquid active compositions.

Thus, the active composition may be a medicinal agent, an agent for treating an internal condition, an agent for treating a mental health condition, an antibiotic active composition, a chemotherapeutic agent, an anti-inflammatory agent, a high molecular weight protein or polypeptide treating agent, or the like. The active composition may also be a nutritional agent.

The invention is broadly applicable to making a wide variety of dosage forms such as tablets, including but not limited to, antacid tablets, cough medicine tablets, sore throat tablets, breath freshener tablets, vitamin tablets, calcium tablets, dietary supplement and nutrient tablets, laxative tablets, cold tablets, analgesic tablets, anti-diarrhea tablets, reducing tablets, pain reliever tablets, sleeping tablets, and many prescription and non-prescription drug and pharmaceutical tablets.

Exemplary medicinal agents include agents for treating cardiovascular conditions such as chlorothiazide (diuretic), propranolol (antihypertensive), hydralazine (peripheral vasodilator), isosorbide or nitroglycerin (coronary vasodilators), metoprolol (beta blocker), procainamide (antiarrythmic), clofibrate (cholesterol reducer) or coumadin (anticoagulant); agents for treating internal conditions such as conjugated estrogen (hormone), tolbutamide (antidiabetic), levothyroxine (thyroid conditions), propantheline (antispasmodic), cimetidine (antacid), phenyl propanolamine (antiobesity), atropine or diphenoxalate (antidiarrheal agents), docusate (laxative), or prochlorperazine (antinauseant); agents for treating mental health conditions such as haloperidol or chlorpromazine (tranquilizers), doxepin (psychostimulant), phenytoin anticonvulsant), levo dopa (antiparkinism), benzodiazepine (antianxiety) or phenobarbital (sedative); anti-inflammatory agents such as fluorometholone, acetaminophen, phenacetin, aspirin, hydrocortisone, or predisone; anti-histamines such as diphenhydramine hydrochloride or dexchlorpheniramine maleate; antibiotics such as sulfanilamide, sulfamethizole, tetracycline hydrochloride, penicillin and its derivatives, cephalosporin derivatives or erythromycin; chemotherapeutic agents such as sulfathiazole, doxorubicin, cisplatin or nitrofurazone; topical anaesthetics such as benzocaine; cardiac tonics such as digitalis or digoxin; antitussives and expectorants such as codeine phosphate, dextromethorphan or isoproterenol hydrochloride; oral antiseptics such as chlorhexidine hydrochloride or hexylresorcinol; enzymes such as lysozyme hydrochloride or dextronase; birth control agents such as estrogen; opthalmic treating agents such as timolol or gentamycin, and the like. In addition, medicinal treating agents may also include whole proteins such as the VP3 capsid protein (also known as the VP Thr and VP1 capsid proteins in other nomenclature systems) of foot-and-mouth disease virus described in U.S. Pat. No. 4,140,763 as being useful as the active ingredient in a vaccine against foot-and-mouth disease, insulin or interferon; polypeptide treating agents such as endorphins, human growth hormone, or bovine growth hormone, or still lower molecular weight polypeptides or conjugates of those polypeptides linked protein carriers as are described in Sutcliffe et al., Science, 219, 660-666 (1983).

Medicaments which are orally administered in accordance with the present invention include, for example, adrenergic agents such as ephedrine, desoxyephedrine, phenylephrine, epinephrine and the like, cholinergic agents such as physostigmine, neostigmine and the like, antispasmodic agents such as atropine, methantheline, papaverine and the like, curariform gents such as chlorisondamine and the like, tranquilizers and muscle relaxants such as fluphenazine, chlorpromazine, triflupromazine, mephenesin, meprobamate and the like, antidepressants like amitriptyline, nortriptyline, and the like, antihistamines such asdiphenhydramine,dimenhydrinate, tripelennamine, perphenazine, chlorprophenazine, chlorprophenpyridamine and the like, hypotensive agents such as rauwolfia, reserpine and the like, cardioactive agents such as bendroflumethiazide, flumethiazide, chlorothiazide, aminotrate, propranolol, nadolol, metoprolol, atenolol, procainamide and the like, angiotensin converting enzyme inhibitors such as captopril and enalapril, bronchodialators such as theophylline, steroids such as testosterone, prednisolone, and the like, antibacterial agents, e.g., sulfonamides such as sulfadiazine, sulfamerazine, sulfamethazine, sulfisoxazole and the like, antimalarials such as chloroquine and the like, antibiotics such as the tetracyclines, nystatin, erythromycin, streptomycin, cephradine and other cephalosporins, penicillin, semisynthetic penicillins, griseofulvin and the like, sedatives such as chloral hydrate, phenobarbital and other barbiturates, glutethimide, antitubercular agents such as isoniazid and the like, analgesics such as aspirin, acetominophen, propoxyphene, meperidine, ibuprofen, and the like, etc. These substances are frequently employed either as the free compound or in a salt form, e.g., acid addition salts, basic salts like alkali metal salts, etc. Other therapeutic agents having the same or different physiological activity can also be employed in pharmaceutical preparations within the scope of the present invention.

The active composition may be used singly or as a mixture of two or more such agents.

Other ingredients that can be present in the compositions of the present invention include breath fresheners and flavors, e.g., spearmint oil, peppermint oil, cinnamaldehyde, cetyl pyridinium chloride, menthol saccharin sodium, glycyrrhizin, malt syrup, citric acid, tartaric acid, lemon oil, citrus flavor, and the like, sodium fluoride and the like, anti-plaque/anti-bacterial compositions suitable to treat or prevent periodontal disease, e.g., chlorobutanol, chlorothymol, chlorohexidine, their salts, and the like, dental pain control ingredients, e.g., benzocaine, lidocaine and the like:

One or more adjuvants may also be included with an active composition. Exemplary of useful adjuvants are chelating agents such as ethylenediaminetetracetic acid (EDTA) that bind calcium ions and assist in passage of medicinal agents through the mucosa and into the blood stream. Another illustrative group of adjuvants are the quaternary nitrogen-containing compounds such as benzalkonium chloride that also assist medicinal agents in passing through the mucosa and into the blood stream.

In addition to the above ingredients, there may also be incorporated other additives selected from among the various pharmaceutically acceptable additives available to the those skilled in the art for the purpose of obtaining desirable processing and physical qualities including enhancement of the dispersibility and stability of the active ingredient. Such additives which can be used in addition to the active ingredient include the following substances: stabilizers/preservatives, e.g., parahydooxybenzoic acid alkyl esters, antioxidants, antifungal agents, and the like; coloring agents, e.g., aluminum lake, titanium dioxide, and the like; excipients/disintegration modulating agents, e.g., magnesium silicate, silicic acid anhydride, aluminum silicate, calcium carbonate, magnesium aluminum metasilicate, calcium hydrogen phosphate, and the like; stearic acid and its salts; palmitic acid; talc; and other substances known as emulsifiers, dispersants, binders, thickeners and the like.

DOSAGE FORMS

A composition of this invention may be provided in a variety of physical forms. For example, a composition may be an intimate mixture of the polymeric system and active composition in either dry form, as a semi-solid or as a liquid suspension. The composition may also be provided as a three-dimensional structure such as a capsule, a capsule aggregate, a film or laminate. When provided as a three-dimensional structure, the active composition is contained in a medicinally inert matrix.

A composition of this invention may also be provided in two parts, a polymer phase containing calcium polycarbophil and other pharmaceutical or other excipients, and a liquid phase containing water and optionally co-solvents. One or more active drugs may be incorporated in either one phase or both of the phases. When the polymer and liquid parts are mixed, "polymerization" ensues.

A composition of this invention may also be provided as a suspension of calcium polycarbophil and optionally other excipients in nonpolar solvents e.g. vegetable oils and synthetic oils, which when it comes into contact with body fluid (water), either through parenteral injection, implantation or local application, will "polymerize" to form a complex hydrogel matrix in situ and provide a controlled release delivery system. Such a system is useful for parenteral and local applications.

The active composition is present in the compositions of this invention in an amount that is sufficient to prevent, cure and/or treat a condition for a desired period of time for which the composition of this invention is to be administered, and such an amount is referred to herein as "an effective amount". As is well known, particularly in the medicinal arts, effective amounts of medicinal agents vary with the particular agent employed, the condition being treated and the rate at which the composition containing the medicinal agent is eliminated from the body, as well as varying with the animal in which it is used, and the body weight of that animal. Consequently, effective amounts of active compositions may not be defined for each agent. Thus, an effective amount is that amount which in a composition of this invention provides a sufficient amount of the active composition to provide the requisite activity of active composition in or on the body of the treated animal for the desired period of time, and is typically less than that amount usually used.

Inasmuch as amounts of particular active compositions in the blood stream that are suitable for treating particular conditions are generally known, as are suitable amounts of active compositions used in cosmetics, it is a relatively easy laboratory task to formulate a series of controlled release compositions of this invention containing a range of such active compositions to determine the effective amount of such an active composition for a particular composition of this invention. While the effective amount for all active compositions cannot be stated, typical compositions of this invention may contain about one microgram to about one gram of active composition per dose administered. More preferably, a composition of this invention may contain about one microgram to about 400 milligrams per dose.

The dosage form can be packaged in unit dose blister packs, pouches in a carton, vials with screw or flip-top lids, bottles with screw or flip-top lids, or any other convenient package form.

POLYCARBOPHIL COMPONENT

Several types of materials are suitable for forming the polycarbophil type composition component. The polymer contains a plurality of a repeating unit of which at least about 80 percent contain at least one carboxyl functionality and about 0.05 to about 1.5 percent cross-linking agent substantially free from polyalkenyl polyether, with the percentages being based upon the weights of the unpolymerized repeating unit and cross-linking agent, respectively. In more preferred practice, at least about 90 percent of the repeating units contain at least one carboxyl functionality, and in still more preferred practice, at least 95 percent of those repeating units contain at least one carboxyl functionality. Most preferably, this material is a reaction product of the polymerization of only a carboxyl-functional monomer and a cross-linking agent. Also in more preferred practice, this component contains about 0.1 to about 1 percent by weight of polymerized cross-linking agent. The material also contains from 5% to 25%, preferably 18% to 22% calcium as a calcium salt of the polymer acid. Certain species of this type of polymer is commercially available under the generic name "calcium polycarbophil".

A calcium polycarbophil type composition polymer useful herein may thus be defined as a reaction product of the copolymerization of at least 80 weight percent monoethylenically unsaturated carboxy-functional monomer and about 0.05 to about 1.5 weight percent of a cross-linking agent free of polyalkenyl polyether and 18-22% of calcium. The remaining monomers that may be present to constitute 100 percent by weight of the monomers.

In addition to the above two ingredients, the polycarbophil type polymer may also include polymerized monoethylenically unsaturated repeating units such as C1-C6 alkyl esters of one or more of the above-described acids such as hexyl acrylate, butyl methacrylate and methyl crotonate; hydroxyalkylene-functional esters of the above-described acids that contain a per molecule average of 1 to about 4 oxyalkylene groups containing 2-3 carbon atoms such as hydroxyethyl methacrylate, hydroxypropyl acrylate and tetraethylene glycol monoacrylate; methacrylamide, acrylamide and their C1-C4 mon- and di-alkyl derivatives such as N-methyl acrylamide, N-butyl methacrylamide and N,N-dimethyl acrylamide; styrene; and the like as are known in the art as being copolymerizable with the above described carboxyl functionality-containing monomers and cross-linking agents. The polymers most preferably are prepared from only the monoethylenically unsaturated carboxy-functional monomer and the cross-linking agent.

The calcium polycarbophil type composition useful herein may be prepared by conventional free radical polymerization techniques utilizing initiators such as benzoyl peroxide, azobisisobutyronitrile, and the like, are polymerized in an aqueous medium, and are not agglomerated by steam action. A particularly preferred polycarbophil component that is commercially available is that material sold under the designation calcium polycarbophil by the B. F. Goodrich Co. of Cleveland, Ohio. The United States Pharmacopeia, 1990 edition, United States Pharmacopeial Convention, Inc., Rockville, Md., at page 218, indicates that calcium polycarbophil is a calcium salt of polyacrylic acid cross-linked with divinyl glycol that has a calcium content of not less than 18% and not more than 22% and absorbs not less than 35 grams of sodium bicarbonate solution per one gram of the powder in the test under "Absorbing Power".

The polycarbophil component must be present in the form of its calcium salt. The divalent cation should be present in an amount from about 5 to about 25 percent and preferably from about 18 to about 22 percent, based on the weight of polycarbophil.

The interaction of the polycarbophil type composition with the water should be at a pH of from about 3 to about 10, preferably at a pH from about 5.5 to about 8.5. Interaction at such a pH will assure that the polycarbophil type composition and water form the desired structure.

The polycarbophil type component may be interacted with the water in any suitable means. Water may be mixed with other cosolvents e.g. glycerol, propylene glycol, or polyethylene glycols, in varying proportion to affect the formation of the polymeric hydrogel.

Prior to interacting the calcium polycarbophil with the water, the active composition as described previously may be incorporated into the polycarbophil type composition. The incorporation may be through dissolution, or dispersion of the active composition in a matrix of the calcium polycarbophil. The amount of polycarbophil type composition will affect the consistency of the final product. Accordingly, the final product may vary from a water-like consistency to that of a solid dry powder. The polycarbophil type composition may be introduced into the reaction as a solid or in a non-aqueous or a mixed solvent system. All percentages expressed in this application are by weight unless stated otherwise.

The interaction of the calcium polycarbophil with the water results in the formation of a complex hydrogel matrix structure which then acts to control the diffusion or other transport of the active composition within and from the matrix itself.

The desired level of controlled or sustained release will vary, depending upon the ratio of the components employed, the physical state of the components of the particular active composition, the method of incorporation, the order of mixing of the components, and the like. Additional additives may also be present which may modify the characteristics of the matrix and its release properties.

GENERAL FORMULATION CONSIDERATIONS

In typical practice, the ratio by weight of the polymeric complex to the active composition in the composition is about 200,000:1 to about 1:100. In preferred practice, however, the weight ratio of polymeric complex to active composition is about 100,000:1 to about 10:1. Those weight ratios are determined using dry ingredients.

In addition to the active composition and polymeric complex, the compositions of this invention may also contain pharmaceutically acceptable diluents and/or one or more materials present as a medicinally inert matrix.

A composition of this invention is an intimate mixture of the polymeric matrix and the active composition and includes mixtures formed at the time of administration by mixing various components. The phrase "intimate mixture" is used herein to mean that the components of the composition are mixed substantially uniformly so that none of those components is localized. A minor amount of agitation immediately prior to use may be required for some liquid compositions of this invention to achieve an intimately mixed state when used. In two part preparations, the polymer phase and the liquid phases are mixed just before application. Once the two phases are mixed, the composition is such as defined above. Alternatively, the polymer composition in nonpolar solvents and cosolvents may be introduced into or onto the body, either parenterally or locally, and the hydrogel formation completed by the water present in the body fluid at the site of application.

METHOD OF TREATMENT

A controlled release method of treatment is also contemplated. According to this method, a controlled release composition of this invention is provided. A composition of the present invention may be placed into the oral, buccal, or gingival area. Alternatively, in the method of controlled release treatment a controlled release composition containing an effective amount of active composition per dose is provided, as described before and may be initially present or may be formed in situ. An area of skin or mucus membrane to be treated is contacted with the provided composition. Each of the beforedescribed compositions may be administered in accordance with this method.

For purposes of in situ formation of the complexes of the present invention, it is necessary to deliver the calcium polycarbophil as a relatively fluid composition, as by parenteral injection. In such instances, the use of water or other liquids capable of initiating hydrogen bonding of the calcium polycarbophil should be avoided. It is generally preferred to use as a carrier for the calcium polycarbophil a liquid which is a nonpolar solvent, such as an animal or vegetable oil, or a synthetic oil, such as a silicone. The carrier for such purposes then is usually hydrophobic. For certain applications, however, it may be possible to employ glycerine, propylene glycol, polyethylene glycols or other mono or polyhydric alcohols as a carrier for the calcium polycarbophil. The calcium polycarbophil may be suspended in the appropriate carrier as small microparticles capable of being parenterally injected or otherwise introduced into a subject.

EXAMPLE 1

This example demonstrates the manufacture of a composition of the present invention which is a controlled release candy composition using calcium polycarbophil and breath freshener. Calcium Polycarbophil, USP (Carbopol EX-83 Resin, Lot No. Z139117, B. F. Goodrich) is used in this example. Other grades of varying particle size and surface area materials of this resin may be used to obtain other desirable properties.

Sixty grams of calcium polycarbophil is mixed with five hundred milligrams of Peppermint Oil, NF. In a separate container, twenty grams of Mannitol, USP are mixed with twenty grams of sodium alginate (Keltone HV, Kelco Co). Additionally, five hundred milligrams of Peppermint Oil, NF are added to this mixture and mixed well.

About forty grams of Purified Water, USP are added to the calcium polycarbophil mixture prepared above and the preparation is mixed well rapidly. The preparation is allowed to gel for about 45 seconds, at which time, the mannitol and sodium alginate mixture prepared above is added and the preparation is mixed well to obtain uniformly wet spongy mass. The mass is then rolled into small spaghetti type rolls and small pieces of about 200 milligrams weight are cut. The pieces are rolled by hand into small balls of about ⅛-¼" diameter. The balls so produced are dried at 37° C. for twenty four hours.

Testing

The dried balls were observed to be of very hard marble type candies. The ball was noted to disintegrate in water maintained at 37° C. over 2-6 hours under mild agitation. The ball was observed to dissolve slowly in the mouth over two to six hours and Peppermint Oil was noted to release over this time period. The ball (candies) was non-gummy, non-sticky and provided a pleasant, mouth freshening over the time period. The candy did not break but dissolved slowly even when it was swished around in mouth constantly.

It is very clear from this experiment that this formulation can serve as a controlled release application for a variety of products. The main reason for the controlled activity is the tendency of calcium polycarbophil to form a rubbery, spongy hydrogel material when mixed with small and limited quantities of water. It appears that water causes internal structurization and "polymerization" by hydrogen bonding. The incorporation of sodium alginate and/or mannitol enables one to achieve the desired breakdown and bonding of the mass. The addition of mannitol is also for achieving the desired taste and cooling effect when the candy is sucked.

EXAMPLE 2

Pour On Burn Dressing Containing Antimicrobial Agent

This example demonstrates the manufacture of a composition of present invention which is supplied as a "two component system" which is suitable as a controlled release pour on dressing for burn treatment. Calcium polycarbophil, USP (Carbopol EX-788 Resin, B. F. Goodrich) is used in this example.

Fifty grams of calcium polycarbophil is sterilized by dry heat sterilization method. The sterile powder, is mixed with five grams of sterile mannitol. The dry powder is packaged into suitable glass containers as "Solid Phase 1". In a separate container, 40 milliliters of sterile solution containing 1% silver nitrate is prepared. To prepare the "pour-on" burn dressing, the silver nitrate solution is added to the calcium polycarbophil/mannitol mixture. The suspension is mixed well to disperse the material and to initiate polymerization. After sixty seconds, the preparation begins to thicken. It is suitable to be slowly poured over the affected area to form an on-site wound dressing.

In the laboratory trial, the dressing was poured onto a flat glass plate. The preparation solidified and appeared dry within less than two minutes and became like a spongy woven fabric. Small pieces of this preparation were cut and submerged in 100 ml. of deionized water (having an electrical resistance of 18 mega ohms) and maintained at 37° C. The samples were gently shaken, continuously. The water was removed and a fresh quantity of water added at specified sampling time intervals. The water samples were tested for the presence and release of silver nitrate. The pieces were found to release silver nitrate at a fairly constant rate over a 72 hour time period. After about 96 hours, silver nitrate was completely released from the matrix. In a separate experiment, the preparation was poured onto a subject's hand. The preparation solidified within a few seconds into a spongy mass. The preparation stayed on without causing any irritation, burning or discomfort and peeled off very easily without causing any pain.

It is very clear from this experiment that this formulation can serve as controlled release application for local and bolus type of applications.

What is claimed is:

1. A polymeric controlled release composition comprising a reaction complex formed by the interaction of (1) a calcium polycarbophil component which is a water-swellable, but water-insoluble, fibrous, cross-linked carboxy-functional polymer, said polymer containing (1) a plurality of repeating units of which at least about 80 percent contain at least one carboxyl functionality, and (b) about 0.05 to about 1.5 percent cross-linking agent substantially free from polyalkenyl polyether, said percentages being based upon the weights of unpolymerized repeating unit and cross-linking agent, respectively, with (2) water, in the presence of an active agent selected from the group consisting of medicinal agents, breath fresheners, and flavors, wherein the amount of calcium polycarbophil present is from about 0.1 to about 99 percent, the amount of active agent present is from about 0.0001 to about 65 percent, by weight, based upon of the composition, and the amount of water present is from about 5 to about 200 percent, based upon the weight of calcium polycarbophil, said interaction being at a pH from about 3 to about 10, and the calcium polycarbophil being originally present, prior to said interaction, in the form of the calcium salt, having a calcium content from about 5 to about 25 percent, based on the weight of the polycarbophil.

2. The composition according to claim 1 wherein said active agent is a medicament.

3. The composition according to claim 2 wherein said polymeric composition also comprises a hydrophilic colloid.

4. The composition according to claim 3 wherein the said polymeric composition also comprises simple or complex carbohydrates or polyols.

5. The composition according to claim 3 wherein said polymeric composition also comprises one or more cosolvents selected from the group consisting of glycerol, propylene glycol and polyethylene glycol.

6. The composition according to claim 3 which is formed by combining a two component system comprising as one component a polymer phase containing calcium polycarbophil and as the second component a liquid phase containing water or optionally other solvents and the complex is formed at the time of use.

7. The composition according to claim 3 which is formed, in situ by combining a polymer phase dispersed in a nonpolar solvent with water from body fluid, when administered parenterally.

8. The composition according to claim 3 wherein at least about 90 percent of said polymer repeating units contain at least one carboxyl functionality.

9. The composition according to claim 3 wherein at least about 95 percent of said polymer repeating units contain at least one carboxyl functionality.

10. The method according to claim 9 wherein said composition comprises an intimate mixture of said reaction complex and said active agent.

11. The composition according to claim 3 wherein said polymer contains about 0.1 to about 1 percent by weight of polymerized cross-linking agent.

12. The composition according to claim 3 wherein said carboxyl functionality is provided by polymerized acrylic acid.

13. The composition according to claim 3 wherein the ratio by weight of said reaction complex to said active agent is from about 200,000:1 to about 1:100.

14. A method of controlled release treatment comprising the steps of:

(a) providing a polymeric complex and a therapeutically effective amount of an active agent contained within said complex, said polymeric complex comprising a reaction complex formed by the reaction of (1) a water-swellable, but water-insoluble, fibrous cross-linked carboxy-functional polymer, said polymer containing (a) a plurality of repeating units of which at least about 80 percent contain at least one carboxyl functionality and (b) about 0.05 to about 1.5 percent cross linking agent substantially free from polyalkenyl polyether, said percentages being based upon the weights of the unpolymerized repeating unit and cross-linking agent, respectively, or a salt thereof, with (2) water, said interaction being performed in the presence of an active agent, selected from the group consisting of medicinal agents, wherein the amount of calcium polycarbophil present is from about 0.1 to about 99 percent, the amount of active agent present is from about 0.0001 to about 65 percent, by weight, based upon the weight of the composition, and the amount of water present is from about 5 to about 200 percent, based upon the weight of calcium polycarbophil, said interaction being at a pH from about 3 to about 10, and the calcium polycarbophil being originally present, prior to said interaction, in the form of the calcium salt, having a calcium content from about 5 to about 25 percent, based on the weight of the polycarbophil; and (b) contacting an area of skin or mucous membrane to be treated with said composition for a period of time that is sufficient to allow a therapeutically effective amount of said active agent to be released from the complex.

* * * * *